(12) United States Patent
Alkordi et al.

(10) Patent No.: US 11,707,726 B2
(45) Date of Patent: Jul. 25, 2023

(54) NITRIC OXIDE CONTAINING COMPOSITE

(71) Applicant: Heart Biotech Nano Limited, Winchester (GB)

(72) Inventors: Mohamed Alkordi, Winchester (GB); Magdi Yacoub, Winchester (GB)

(73) Assignee: HEART BIOTECH NANO LIMITED, London (GB)

( * ) Notice: Subject to any disclaimer, the term of this patent is extended or adjusted under 35 U.S.C. 154(b) by 82 days.

(21) Appl. No.: 16/191,487

(22) Filed: Nov. 15, 2018

(65) Prior Publication Data
US 2019/0143295 A1    May 16, 2019

(30) Foreign Application Priority Data

Nov. 15, 2017 (GB) ..................................... 1718871

(51) Int. Cl.

| | |
|---|---|
| *B01J 20/10* | (2006.01) |
| *A61K 9/14* | (2006.01) |
| *A61K 9/50* | (2006.01) |
| *A61K 8/19* | (2006.01) |
| *A61P 9/00* | (2006.01) |
| *A61K 8/25* | (2006.01) |
| *A61K 8/28* | (2006.01) |
| *A61K 8/02* | (2006.01) |
| *A61K 8/41* | (2006.01) |
| *A61Q 19/00* | (2006.01) |
| *C01B 33/18* | (2006.01) |
| *B01J 20/22* | (2006.01) |
| *B01J 20/28* | (2006.01) |
| *B01J 20/32* | (2006.01) |
| *A61K 33/00* | (2006.01) |
| *C07F 7/00* | (2006.01) |

(52) U.S. Cl.
CPC ............ *B01J 20/103* (2013.01); *A61K 8/0241* (2013.01); *A61K 8/19* (2013.01); *A61K 8/25* (2013.01); *A61K 8/28* (2013.01); *A61K 8/41* (2013.01); *A61K 9/143* (2013.01); *A61K 9/145* (2013.01); *A61K 9/501* (2013.01); *A61P 9/00* (2018.01); *A61Q 19/00* (2013.01); *B01J 20/223* (2013.01); *B01J 20/28016* (2013.01); *B01J 20/28057* (2013.01); *B01J 20/28085* (2013.01); *B01J 20/3214* (2013.01); *C01B 33/18* (2013.01); *A61K 33/00* (2013.01); *A61K 2800/412* (2013.01); *A61K 2800/413* (2013.01); *A61K 2800/624* (2013.01); *A61K 2800/651* (2013.01); *C01P 2004/61* (2013.01); *C07F 7/00* (2013.01)

(58) Field of Classification Search
None
See application file for complete search history.

(56) References Cited

U.S. PATENT DOCUMENTS

| | | | |
|---|---|---|---|
| 6,287,332 B1 * | 9/2001 | Bolz .......................... | A61F 2/82 |
| | | | 623/1.12 |
| 2017/0018245 A1 | 1/2017 | Park et al. | |
| 2017/0182453 A1 * | 6/2017 | Mu ........................ | B01D 53/04 |

FOREIGN PATENT DOCUMENTS

| | | |
|---|---|---|
| CN | 103157441 | 6/2013 |
| CN | 105668548 | 6/2016 |
| CN | 106984273 | 7/2017 |

OTHER PUBLICATIONS

Huang et al., "Magnetic Zr—MOFs nanocomposites for rapid removal of heavy metal ions and dyes from water", Chemospehere, 199, 2018.
Seabra et al., "New strategy for controlled release of Nitric Oxide", Journal of Nano Research: JNanoR, vol. 20., 61-67, publication year: 2012.
Zhang et al., :One-pot synthesis of UiO-66@SiO2-shell core microspheres as stationary phase for high-performance liquid chromatography, RSC Advances, vol. 5, No. 2, 1043-1050, publication year: 2015.
Lowe et al., "Storage and delivery of nitric oxide via diazeniumdiolated metal organic framework", Microporous and Mlesoporous Materials, 181, 17-22, publication year: 2013.
Lee, et al. "UiO-66-NH2 Metal-Organic Framework (MOF) Nucleation on TiO2, ZnO, and Al2O3 Atomic Layer Deposition-Treated Polymer Fibers: Role of Metal Oxide on MOF Growth and Catalytic Hydrolysis of Chemical Warfare Agent Simulants." ACS Appl Mater Interfaces. 2017;9(51):44847-44855. doi:10.1021/acsami. 7b15397.
Mohamed et al., "Chemical and biological assessment of metal organic framework (MOFs) in pulmonary cells and in an acute in vivo model: relevance to pulmonary arterial hypertenision therapy", Pulmonary Circulation, 7, 435-444, Jun. 27, 2017.
Haikal et al., "Controlling the uptake and regulating the release of nitric oxide in microporous solids", Applied Materials and Interfaces, 9, 43520-43528, Nov. 28, 2017.
Ingleson, et al. "Nitric Oxide Chemisorption in a Postsynthetically Modified Metal Organic Framework", Inorganic Chemistry, vol. 48, No. 21, 9986-9988, Oct. 1, 2009.

(Continued)

*Primary Examiner* — Katherine Peebles
(74) *Attorney, Agent, or Firm* — Tarolli, Sundheim, Covell & Tummino L.L.P.

(57) ABSTRACT

The present invention provides a nitric-oxide containing composite in the form of microparticles, wherein said microparticles comprise:
(i) a core which comprises silica;
(ii) a layer on said core which comprises a metal-organic framework; and
(iii) nitric oxide;
wherein said metal-organic framework comprises organic ligands comprising at least one amine group, said metal-organic framework is uniformly distributed on the surface of said silica core and said nitric oxide is chemisorbed within said metal-organic framework.

19 Claims, 6 Drawing Sheets

(56) References Cited

OTHER PUBLICATIONS

Stevens et al. "Nitric Oxide-Releasing Silica Nanoparticle Inhibition of Ovarian Cancer Cell Growth", Molecular Pharmaceutics, vol. 7, No. 3, 775-785, Mar. 5, 2010.
Nguyen, "Postsynthetic diazeniumdiolate formation and NO release from MOFs", Crystengcomm, vol. 12, No. 8, 2335, Apr. 10, 2010.
Tuanwei Liu et al., "Silica/polymer microspheres and hollow polymer microspheres as scaffolds for nitric oxide release in PBS buffer and bovine serum", Polymer Chemistry, vol. 6, No. 9, 1512-1520, Dec. 2, 2014.
Shin et al., "Synthesis of Nitric Oxide-releasing Silica Nanoparticles", Journal of the American Chemical Society, vol. 129., No. 15, 4612-4619, Mar. 22, 2007.
Peikert et al., "Tuning the Nitric Oxide Release Behaviour of Amino Functionalised HKUST-1", Microporous and Mesoporous Materials, vol. 216., 118-126, Nov. 1, 2015.
Non Final Office Action for Corresponding U.S. Appl. No. 16/191,487, dated Aug. 8, 2022, pp. 1-19.

* cited by examiner

NITRIC OXIDE CONTAINING COMPOSITE

INTRODUCTION

The present invention relates to a composite in the form of microparticles which comprise a core comprising silica, a layer on the core comprising a metal-organic framework and nitric oxide, wherein the nitric oxide is chemisorbed within the metal-organic framework. The invention also relates to a method of making the composite which generates a highly uniform distribution of the metal-organic framework on the surface of the silica core. The invention further relates to a pharmaceutical composition and to a dosage form comprising the composite as well as to medical uses of the composite.

BACKGROUND

Nitric oxide is produced in vivo from L-arginine via the enzyme nitric oxide synthase. It is a crucial biological agent in the cardiovascular, nervous and immune systems. For instance, nitric oxide synthesised by endothelial cells that line blood vessels mediates processes such as vasodilation, inhibition of platelet and inflammatory cell activation. Nitric oxide is also a neurotransmitter and neuromodulator in the peripheral and central nervous systems and it contributes to the cytotoxic effects of inflammatory cells on pathogens. Deficiencies in nitric oxide levels have been linked to a wide range of different diseases including, for example, cancer, cardiovascular disease, e.g. pulmonary arterial hypertension, atherosclerosis, thrombotic disorders and coronary heart disease, neurological disease and bacterial infection.

Currently, when nitric oxide must be administered as part of a medical treatment, it is delivered in the form of a gas. This means that treatment must be carried out in dedicated care facilities equipped to monitor the treatment. This is due to the risks associated with the use of high pressure nitric oxide canisters and the toxicity of nitric oxide above certain concentrations. The range and diversity of the effects of nitric oxide, in fact, limit current use of nitric oxide therapeutically. To overcome this problem, materials are required that can store significant quantities of nitric oxide and then release it to specific sites in the body. Even more demanding, are materials capable of storing nitric oxide at ambient conditions (e.g. pressure, temperature and relative humidity) for safe and ease delivery of nitric oxide (e.g. inhalers, aerosol dispensers, patches), circumventing the limitations to treatment imposed by need for high pressure canisters that are not safe to transport and handle.

As a result of the realisation of the role in nitric oxide deficiency in a range of diseases and limitations in the current mode of treatment with gaseous nitric oxide, there has been significant interest in developing materials that can safely store nitric oxide as well as provide controlled and safe delivery of nitric oxide in therapeutically effective levels. A lot of attention has focussed on the provision of NO donors. Many different classes of donors exist but the N-diazeniumdiolates (NONOates) have received the most attention due to their ability to spontaneously release NO in physiological media. NONOates have the advantage of being relatively inexpensive molecular solids, but they suffer the disadvantage that the NO releases upon contact with moisture. As a result, NONOates do not provide a practical storage solution for nitric oxide.

Another example of a solid sorbent that has been explored for nitric oxide storage and delivery is metal-exchanged zeolites. In such zeolites, the NO is typically chemisorbed to cations until it is displaced with a nucleophile, e.g. water. As with NONOates, however, the water-sensitivity means that the NO releases almost immediately upon contact with water.

Metal-organic frameworks have also been examined for their potential in NO sorption and release. M-CPO-27 and HKUST-1, for example, have both previously been shown to adsorb, store and release nitric oxide.

SUMMARY OF THE INVENTION

Viewed from a first aspect the present invention provides a nitric oxide-containing composite in the form of microparticles, wherein said microparticles comprise:
(i) a core which comprises silica;
(ii) a layer on said core which comprises a metal-organic framework; and
(iii) nitric oxide;
wherein said metal-organic framework comprises organic ligands comprising at least one amine group, said metal-organic framework is uniformly distributed on the surface of said silica core and said nitric oxide is chemisorbed within said metal-organic framework.

Viewed from a further aspect the present invention provides a composite in the form of microparticles, wherein said microparticles comprise:
(i) a core which comprises silica; and
(ii) a layer on said core which comprises a metal-organic framework;
wherein said metal-organic framework comprises an organic ligand comprising at least one amine group and said metal-organic framework is uniformly distributed on the surface of said silica core.

Viewed from a further aspect the present invention provides a method of making a composite as hereinbefore described, comprising:
(i) mixing silica microparticles and precursors for the preparation of a metal-organic framework, wherein said precursors comprise metal ions and an organic ligand comprising at least one amine group to form a mixture;
(ii) stirring said mixture; and
(iii) obtaining said composite.

Viewed from a further aspect, the present invention provides a method of making a nitric oxide-containing composite as hereinbefore described, comprising:
(i) preparing a composite as hereinbefore described;
(ii) contacting said composite with nitric oxide under pressure; and
(iii) obtaining said nitric oxide-containing composite.

Viewed from a further aspect the present invention provides a pharmaceutical composition comprising a nitric oxide-containing composite as hereinbefore described.

Viewed from a further aspect the present invention provides a dosage form comprising a nitric oxide-containing composite as hereinbefore described.

Viewed from a further aspect the present invention provides a nitric oxide-containing composite as hereinbefore described for use in medicine.

Viewed from a further aspect the present invention provides a nitric oxide-containing composite as hereinbefore described for use in the treatment of nitric oxide-mediated disease.

Viewed from a further aspect the present invention provides the use of a nitric oxide-containing composite as hereinbefore described for the manufacture of a medicament for the treatment of nitric oxide-mediated disease.

Viewed from a further aspect the present invention provides a method of treatment of a nitric-oxide mediated disease in a subject in need thereof, comprising administering a therapeutically effective amount of a nitric-oxide containing composite as hereinbefore described; and subsequently triggering the release of nitric oxide from said composite.

Definitions

As used herein the term "microparticles" refers to substantially spherical (e.g. spherical) particles having a diameter in the range 1 to 1000 μm.

As used herein the term "average diameter" refers to the mean average diameter.

As used herein the term "metal-organic framework" refers to a two- or three-dimensional structure comprising of metal-containing secondary building units or metal clusters coordinated or bonded to organic ligands. The organic ligands act as linkers between metal ions or clusters.

As used herein the term "chemisorbed" refers to the binding of a substance, in this case nitric oxide, to the surface of another surface (i.e. silica) by the formation of a chemical bond.

As used herein the term "alkyl" refers to saturated, straight chained, branched or cyclic groups. Alkyl groups may be substituted or unsubstituted.

As used herein the term "halide" refers to atoms selected from the group consisting of F, Cl, Br and I.

As used herein the term "aromatic ring" refers to a planar ring that has 4n+2 pi electrons, wherein n is a non-negative, non-zero integer.

As used herein the term "heteroaromatic ring" refers to an aromatic ring in which one or more ring carbon atoms are replaced by at least one hetero atom such as —O—, —N— or —S—.

As used herein, the term "nitric-oxide mediated disease" refers to a disease caused by a nitric-oxide deficiency.

DETAILED DESCRIPTION

The present invention relates to a nitric-oxide containing composite in the form of microparticles, wherein said microparticles comprise:
(i) a core which comprises silica;
(ii) a layer on said core which comprises a metal-organic framework; and
(iii) nitric oxide;
wherein the metal-organic framework comprises organic ligands comprising at least one amine group, the metal-organic framework is uniformly distributed on the surface of the silica core and the nitric oxide is chemisorbed within said metal-organic framework.

The composite of the present invention comprises a silica core and a layer, preferably an outer layer, of a metal-organic framework. The presence of the silica in the composite improves the handling of the composite in medical applications and improves its storage stability. The metal-organic framework provides the storage and controlled release mechanism for the nitric oxide.

A key feature of the nitric-oxide containing composite of the present invention is that the metal-organic framework is uniformly distributed on the surface of the silica core. Preferably the metal-organic framework completely covers the surface of the silica core. Thus preferably the metal-organic framework covers 90-100%, more preferably 95-100% and still more preferably 99-100% of the surface of the core, based on the total surface area of the core. The uniform distribution of the metal-organic framework on the silica core means that a consistent amount of metal-organic framework, and therefore nitric oxide, is provided per unit area, volume or mass of the composite. This means that improved controlled release of nitric oxide from the composite may ultimately be achieved.

A uniform distribution of the metal-organic framework on the surface of the silica is achieved because the metal-organic framework is in the form of nanocrystals having an average diameter of 1-200 nm, more preferably 10-100 nm and still more preferably 20-50 nm. The relatively small and uniform size of the metal-organic framework nanocrystals enables them to pack efficiently and thereby to form a uniform layer on the silica surface. The method employed to prepare the composite of the invention, which is described below in detail, ensures that relatively small nanocrystals of metal-organic framework are formed. Moreover, the presence of silica particles within the initial solution used to construct the metal-organic framework nanoparticles enables the in-situ, spontaneous nucleation and growth of the metal-organic framework nanoparticles and much greater adherence and coverage over the surface of the silica particles, as compared to preparing the metal-organic framework separately and attempting to subsequently load it onto silica particles. Furthermore the nanocrystals of metal-organic framework have a narrow particle size distribution which enables a uniform distribution of the metal-organic framework to form on the surface of the silica core to be formed.

The uniform distribution of the metal-organic framework on the silica core may be observed by SEM and TEM imaging. The uniform distribution of the metal-organic framework may also be quantitatively measured by SEM and also by EDX. In preferred composites of the present invention the metal-organic framework has a uniform distribution (i.e. complete and homogeneous coverage of the silica particles) over the silica particles as shown by the EDX carbon map and EDX elemental map.

Preferably the layer of metal-organic framework on the surface of the silica core has a thickness of 2-200 nm, more preferably 5-100 nm and still more preferably 10-50 nm. Preferably the metal-organic framework forms a monolayer on the surface of the silica core.

In the nitric-oxide containing composites of the present invention, the metal-organic framework has a highly porous structure. Preferably the nitric-oxide containing composite of the invention has a porosity of 100-2000 $m^2/g$, more preferably a porosity of 200 to 1500 $m^2/g$ and still more preferably 300 to 1200 $m^2/g$. Preferred nitric oxide-containing composites of the invention have an average pore diameter of 1 to 100 Angstrom, more preferably 2 to 50 Angstrom and still more preferably 5 to 20 Angstrom. The porosity of the metal-organic framework enables the composite to host therapeutically effective amounts of nitric oxide. At least some of the nitric oxide is chemisorbed in the metal-organic framework. Preferably this is achieved by the nitric oxide forming covalent bonds with one or more atoms present in the metal-organic framework. Particularly preferably the metal-organic framework, and more preferably the organic ligands therein, comprise an amine group which reacts with the nitric oxide to form stable chemical entities and thereby prevent the leaching out of nitric oxide from the composites of the invention.

In preferred nitric-oxide containing composites of the present invention the core consists of silica. Preferably the core has an average diameter of 1-200 μm, more preferably 1-100 μm and still more preferably 1-50 μm. The silica preferably has a surface area of 10-1000 m²/g, more preferably 100-700 m²/g and still more preferably 200-600 m²/g. Suitable silica particles for use in the compositions of the present invention are commercially available.

The presence of the silica core in the nitric-oxide containing composites of the present invention is advantageous for both the storage of the composite and for its use in medical applications. Silica is hygroscopic and therefore improves the stability of the composite and increases its potential shelf life. The relative weight of the silica in the composite eases the handling of therapeutically effective amounts of composite, without compromising the homogeneity or reliability of the end product. Additionally, the presence of silica as filler eases the handling, manufacturing, and packaging process.

In preferred nitric-oxide containing composites of the present invention the metal-organic framework comprises an organic ligand of formula (I)

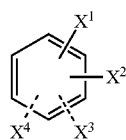
(I)

wherein

----- represents a bond which may be absent or present;

$X^1$ is independently selected from $NH_2$ and NHR, wherein R is $C_{1-8}$ alkyl or $C_{5-10}$ aryl; and each of $X^2$, $X^3$ and $X^4$ are independently selected from COOH, OH, OR, SH, SR, $NH_2$, NHR, $NR_2$, $NO_2$, halide, $C_{1-6}$ alkyl, $OC_{1-6}$alkyl, $C_{5-10}$ aryl, heteroaryl, $SO_3R$ and $SO_3H$, wherein R is $C_{1-8}$ alkyl or $C_{5-10}$ aryl.

In some ligands of formula (I), the aromatic ring is at least substituted at positions 1 and 4 or at positions 1 and 3, i.e. in a para and meta arrangement respectively. Preferably $X^1$ is $NH_2$.

Preferred organic ligands are of formula (II):

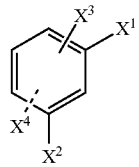
(II)

wherein

----- represents a bond which may be absent or present;

$X^1$ is independently selected from $NH_2$ and NHR, wherein R is $C_{1-8}$ alkyl or $C_{5-10}$ aryl; and each of $X^2$, $X^3$ and $X^4$ are independently selected from COOH, OH, OR, SH, SR, $NH_2$, NHR, $NR_2$, $NO_2$, halide, $C_{1-6}$ alkyl, $OC_{1-6}$alkyl, $C_{5-10}$ aryl, heteroaryl, $SO_3R$ and $SO_3H$, wherein R is $C_{1-8}$ alkyl or $C_{5-10}$ aryl.

Preferably $X^1$ is $NH_2$.

Further preferred organic ligands are of formula (III):

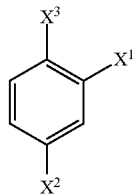
(III)

wherein $X^1$ is independently selected from $NH_2$ and NHR wherein R is $C_{1-8}$ alkyl or $C_{5-10}$ aryl;

and each of $X^2$ and $X^3$ are independently selected from COOH, OH, OR, SH, SR, $NH_2$, NHR, $NR_2$, $NO_2$, halide, $C_{1-6}$ alkyl, $OC_{1-6}$alkyl, $C_{5-10}$ aryl, heteroaryl, $SO_3R$ and $SO_3H$, wherein R is $C_{1-8}$ alkyl or $C_{5-10}$ aryl.

Preferably $X^1$ is $NH_2$.

In preferred organic ligands of formulae (I), (II) and (III), each $X^2$ and $X^3$ are independently selected from COOH, OH and $NH_2$ and more preferably each of $X^2$ and $X^3$ are COOH.

Yet further preferred organic ligands are of formula (IV):

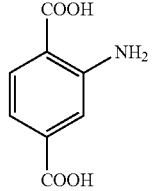 [SMILES: Nc1cc(C(=O)O)ccc1C(=O)O]

Particularly preferred nitric oxide-containing composites of the present invention comprise the metal-organic framework referred to as UiO-66-$NH_2$.

In preferred nitric-oxide containing composites of the present invention the metal-organic framework further comprises metal containing secondary building units and preferably a metal-containing secondary building unit selected from multinuclear metal oxide, carboxylate, hydroxide and halide clusters. The metal-containing secondary building units are formed from metal ions in a solvothermal reaction. In preferred nitric-oxide containing composites of the present invention the metal-containing secondary building unit comprises a metal selected from a Zr, Hf, Ti, Zn, Cr, In, Ga, Cu, Fe, Mo, Cr, Co, Ru, Na, Mg, Mn, Ni, W, Al and V. Yet more preferably the metal-containing secondary building unit comprises a metal selected from Zr, Hf and Ti. Still more preferably the metal-containing secondary building unit comprises Zr or Hf, particularly Zr.

Particularly preferably the metal-containing secondary building unit is selected from:

$M_4O(CO_2)_6$ (a)
$M_3O(CO_2)_6$ (b)
$M_2(CO_2)_4$ (c)
$M_6C_4(OH)_4$—$(CO_2)_{12}$ (d)
$M_6C_8(CO_2)_8$ (e)
$M_3C_3(CO_2)_3$ (f)
$M(C_5HO_4N_2)_4$ (g)

$M(OH)_2(SO_3)_3$ (h)

$M_2(CNS)_4$ (i)

$M(C_3H_3N_2)_4$ (j)

$M(C_3H_3N_2)_8$ (k)

wherein M is a metal ion, preferably a metal selected from Zr, Hf, Ti, Zn, Cr, In, Ga, Cu, Fe, Mo, Cr, Co, Ru, Na, Mg, Mn, Ni, W, Al and V and more preferably from Zr, Hf or Ti and particularly Zr.

Still more preferably the metal-containing secondary building unit is $M_6C_4(OH)_4$—$(CO_2)_{12}$ and especially preferably $Zr_6O_4(OH)_4$—$(CO_2)_{12}$.

Preferred nitric-oxide containing composites of the present invention comprise 10 to 80 wt %, more preferably 20 to 70 wt % and still more preferably 30 to 60 wt % metal-organic framework, based on the total weight of the composite. Preferred composites of the present invention comprise 20 to 90 wt %, more preferably 30 to 80 wt % and still more preferably 40 to 70 wt % silica, based on the total weight of the composite.

The nitric oxide-containing composite of the present invention is preferably in the form of microparticles having an average diameter of 1 to 250 μm, more preferably 1 to 150 μm and still more preferably 1 to 75 μm.

The present invention also relates to a composite in the form of microparticles for preparing the above-described nitric oxide-containing composite. Thus the invention also relates to a composite in the form of microparticles, wherein said microparticles comprise:

(i) a core which comprises silica; and (ii) a layer on said core which comprises a metal-organic framework;

wherein said metal-organic framework comprises an organic ligand comprising at least one amine group and the metal-organic framework is uniformly distributed on the surface of the silica core.

Preferred features of this intermediate composite are as described above for the nitric oxide-containing composite. Thus preferably the metal-organic framework is uniformly distributed on the surface of the silica core as described above in relation to the nitric oxide-containing composite. In other words, preferably the layer is as described above in relation to the nitric-oxide containing composite. Preferably the silica core is as described above in relation to the nitric-oxide containing composite. Preferably the nature of the metal-organic framework is as described above in relation to the nitric oxide containing composite. Preferably the microparticles are as described above in relation to the nitric oxide containing composite.

Preferred intermediate composites of the present invention comprise 10 to 80 wt %, more preferably 20 to 70 wt % and still more preferably 30 to 60 wt % metal-organic framework, based on the total weight of the composite. Preferred composites of the present invention comprise 30 to 80 wt %, more preferably 30 to 80 wt % and still more preferably 40 to 70 wt % silica, based on the total weight of the composite.

As mentioned above, the composites of the present invention are prepared by methods which yield a uniform distribution of metal-organic framework on the surface of the silica core. The methods of the invention preferably comprise a solvothermal synthesis. The method comprises:

(i) mixing silica particles and precursors for the preparation of a metal-organic framework, wherein said precursors comprise metal ions and an organic ligand comprising at least one amine group to form a mixture;

(ii) stirring the mixture; and (iii) obtaining the composite.

Preferably the mixture also comprises a solvent. Preferably the solvent is selected from water, acetone, ethanol, isorpopanol, tetrahydrofuran, ethers, glycol ethers, dimethylsulfoxide, dimethylformamide, acetonitrile, acetamide, toluene, dimethylacetamide, dioxane and combinations thereof. Preferably the solvent is dimethylformamide.

In preferred methods of the invention, an acid is present in the reaction mixture. It has been found that the acid contributes to the provision of a composite with a uniform distribution of metal-organic framework on the silica surface. Preferably the acid is an inorganic acid and more preferably the acid is selected from hydrochloric acid, sulfuric acid, nitric acid and phosphoric acid. Alternatively the acid may be an organic acid, e.g. benzoic acid or acetic acid. Preferably the concentration of acid in the mixture comprising silica, precursors for the preparation of a metal-organic framework (i.e. metal ions and organic ligands comprising at least one amine group), acid and solvent is 0.2-1 M, more preferably 0.5-0.9 M and still more preferably 0.6-0.8 M. Without wishing to be bound by theory, it is thought that the acid may improve the uniform distribution of metal-organic framework on the silica surface by assisting the formation of metal clusters prior to linker binding.

Preferred methods of the invention further comprise preparing a first mixture comprising silica, organic ligand comprising at least one amine group and a first solvent and a second mixture comprising metal ions, a second solvent and preferably acid. In yet further preferred methods the second mixture is added to the first mixture. Thus in a preferred method of the present invention, a second mixture comprising metal ions, a second solvent and preferably acid is added, e.g. dropwise, to a first mixture. Preferably the first mixture is stirred during the addition of the second mixture. Preferably the first and second solvents are the same. Representative examples of suitable solvents include water, acetone, ethanol, isorpopanol, tetrahydrofuran, ethers, glycol ethers, dimethylsulfoxide, dimethylformamide (DMF), acetonitrile, acetamide, toluene, dimethylacetamide, dioxone and combinations thereof. Preferably the solvent is DMF.

Preferably the mixture of silica, precursors for the preparation of a metal-organic framework (i.e. metal ions and organic ligands comprising at least one amine group), solvent and preferably acid are stirred vigorously. It has been found that vigorous stirring of the mixture during formation of the composite is important to arrive at homogeneously deposited metal-organic framework over the silica core. This was also important to yield composites of high porosity as well as composites with desirable pore size and pore size distribution. Particularly preferably the mixture comprising silica, precursors for the preparation of a metal-organic framework (i.e. metal ions and organic ligands comprising at least one amine), solvent and preferably acid is stirred mechanically to achieve a homogeneous mixture. More preferably the mixture is stirred with a stirrer bar at a stirring speed of 100-1000 rpm, more preferably 200-800 rpm and still more preferably 300-500 rpm.

In preferred methods of the invention the concentration of metal ions in the mixture comprising silica, precursors for the preparation of a metal-organic framework (i.e. metal ions and organic ligands comprising at least one amine group), solvent and preferably acid is 10-50 mM, more preferably 20-45 mM and still more preferably 30-40 mM. In further preferred methods of the invention the concentration of organic ligands in the mixture comprising silica, precursors for the preparation of a metal-organic framework (i.e. metal ions and organic ligands comprising at least one amine group), solvent and preferably acid is 14-70 mM, more preferably 28-63 mM and still more preferably 42-56 mM. Preferably the mole ratio of organic ligands to metal ions in the stirred mixture is about 2:1, more preferably about 1.5:1 and still more preferably about 1.3:1.

In preferred methods of the invention the mixing and stirring steps are carried out a temperature of 80-150° C., more preferably 80-120° C. and still more preferably 80-90° C. In further preferred methods of the invention the mixing and stirring steps are carried out for 10-24 hours, more preferably 12-18 hours and still more preferably 12-15 hours. Suitable organic ligands comprising at least one amine group, metal compounds, e.g. metal salts, acids and solvent for use in the methods and composites of the invention are commercially available.

The method of the present invention is advantageously a one-pot approach in which no alteration of the precursors for the metal-organic framework is needed in order to provide the nitric oxide storage and release properties. The method for preparing a nitric oxide-containing composite comprises:
(i) preparing a composite as hereinbefore described;
(ii) contacting the composite with nitric oxide under pressure; and
(iii) obtaining the nitric oxide-containing composite.

Preferably the composite as hereinbefore described is contacted with nitric oxide at a pressure of 1-50 bar, more preferably 2-20 bar and still more preferably 5-10 bar. During contacting with nitric oxide, the nitric oxide is chemisorbed so once the pressure is released nitric oxide remains in the composite.

The nitric oxide-containing metal-organic framework of the composites of the present invention advantageously comprises therapeutically effective amounts of nitric oxide. Preferably 1-25% wt, more preferably 2-20% wt, and still more preferably 9-18% wt of the nitric oxide present in the metal-organic framework of the composite of the present invention is chemisorbed therein. The remainder of the nitric oxide is preferably trapped inside the porous structure of the metal-organic structure. Without wishing to be bound by theory, it is thought that the nitric oxide is chemisorbed to the metal-organic framework by its reaction with amines in the organic ligands, and in particular, by the formation of N-diazeniumdiolate NO donors. A significant advantage of the composite of the present invention is the stability of the N-diazeniumdiolate NO donor within the composite structure. In particular it does not undergo decomposition upon exposure to moisture. Advantageously this means that nitric oxide release is not easily triggered accidentally, e.g. during storage.

Preferably the N-diazeniumdiolate NO donor within the composite structure does not undergo decomposition at any pH above 6. Advantageously the release of nitric oxide from the composite of the invention is triggered by exposure to acid. More preferably the release of NO from the composite is triggered by exposure to a pH of <6, more preferably <5.5 and still more preferably <5.0.

The nitric oxide-containing composites of the invention therefore have numerous advantages including: (i) ability to store large quantities of NO; (ii) stability to moisture and physiological pH; (iii) ease of handling and (iv) acid-triggerable NO release characteristics. As such the nitric oxide-containing composite of the present invention clearly has potential applications in medicine for use in the treatment of nitric-oxide mediated disease. Advantageously the nitric oxide-containing composite of the invention provides controlled-release of nitric oxide. Thus the composite advantageously provides a means to temporarily store the nitric oxide as well as a means to release the nitric oxide in a controlled way.

Representative examples of nitric oxide-mediated diseases include cancer, cardiovascular disease, e.g. pulmonary arterial hypertension, atherosclerosis, thrombotic disorders and coronary heart disease, neurological disease and bacterial infection

DETAILED DESCRIPTION OF THE FIGURES

The invention will now be described with reference to the following non-limiting examples and Figures, wherein.

EXAMPLES

Figure 1:
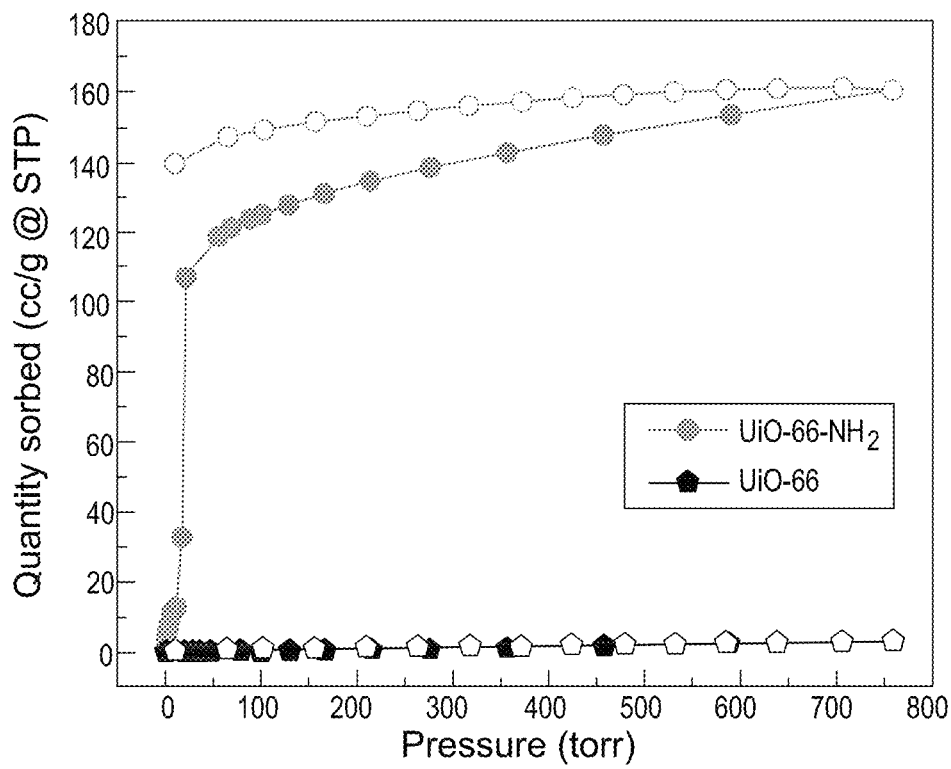
FIG. 1 shows the nitric oxide sorption isotherms for UiO-66 and UiO-66-$NH_2$. Adsorption (closed symbol) and desorption (open symbols)

The examples were performed using the following materials and equipment, unless otherwise stated:

Reagents

Laboratory grade chemicals and reagents were purchased from Sigma-Aldrich or Fisher Scientific and used as received without further purification. Diethylamine NONOate sodium salt hydrate, was purchased from Sigma-Aldrich and used as received.

Equipment

Infrared absorption spectra were recorded using a Thermoscientific Nicoletis-10.

X-ray powder diffraction patterns were recorded on XRD measurements were conducted on PanAlytical diffractometer with Cu source ($\lambda$=1.5406 Å) operated at 30 kV and 40 mA.

Scanning electron microscopy images were acquired on a Nova NanoSEM 450.

Transmission electron microscopy images were acquired on JEOL JEM-2100 at 200 KV.

Energy-dispersive X-ray photoelectron spectroscopy was carried out on a Nova NanoSEM 450 equipped with EDAX Octane Silicon Drift Detector (SDD).

Gas sorption analysis was conducted on a Micrometrics ASAP2020. The surface areas were determined from the nitrogen adsorption isotherms collected at 77 K by applying the Brunauer-Emmett-Teller and Langmuir models. Pore size analysis was conducted using the DFT model of cylindrical pores in oxide surface using the early adsorption data points in the corresponding isotherms.

Preparation of UiO-66-NH$_2$@Silica

In a scintillation vial, a mixture of 2-aminoterephthalic acid (135.86 mg, 0.75 mmol) and silica (100 mg) were mixed and sonicated in 10 ml DMF for 5 minutes. A separately prepared solution of ZrCl$_4$ (125.8 mg, 0.54 mmol) in 5 ml DMF and 1 ml HCl 37% was then added. The vial was capped and the mixture was stirred vigorously at 400 rpm with a stirrer bar (1 cm) for 12 hrs at 80° C., then filtered and washed with ACN, then exchanged in heated ACN at 80° C. under autogenous pressure for 2 hrs. The powder was filtered then dried in an isothermal oven at 80° C. for 2 hours yielding 230 mg of UiO-66-NH$_2$@Silica (81.5% yield).

For comparison purposes, samples of UiO-66 and UiO-66-NH$_2$ were also prepared by conventional techniques.

Example 1 Treatment of UiO-66, UiO-66-NH$_2$ and UiO-66-NH$_2$@Silica Samples Under a High Pressure Nitric Oxide Atmosphere Each sample (30 mg) was placed in a closed Eppendorf tube and sealed. The Eppendorf tube caps were punctured with a needle to enable efficient gas exchange and transferred to a BuchiGlasuster miniclave stainless steel pressure reactor, equipped with Teflon inserts and a pressure gauge. The pressure reactor was flushed with nitrogen gas, then filled with nitric oxide gas to a pressure of 10 bar (BOC, AK 35 bar Nitric Oxide N2.5) at room temperature for 12 hours. After this time, the nitric oxide pressure was gradually vented in a fume hood, and the pressure reactor was flushed with nitrogen at a pressure of 10 bar. The pressure reactor was then opened to the air and the samples transferred to a desiccator for the nitric oxide release study.

Example 2 Gas Sorption Isotherms

FIG. 1 shows the nitric oxide sorption isotherms for UiO-66 and UiO-66-NH$_2$ at various pressures. UiO-66-NH$_2$ demonstrated a large increase in the amount of nitric oxide absorbed at low pressures. The amount of nitric oxide absorbed further increased to 160 cm$^3$/g when the pressure was increased to 760 torr (1 bar). In contrast, UiO-66 demonstrated very limited sorption capability towards nitric oxide.

It was not possible to remove all of the nitric oxide absorbed by UiO-66-NH$_2$ after the first nitric oxide sorption isotherm, due to pronounced desorption hysteresis. These data indicate that nitric oxide was either trapped or chemisorbed within the metal-organic framework structure.

The nitric oxide uptake for UiO-66-NH$_2$ was calculated to be 6.98 mmol/g (based on a formula unit of ZrO$_5$C$_8$NH$_5$, a calculated molecular mass of 286.35 g/mol, 3.49 mmol/g of primary amine groups and two nitric oxide molecules chemisorbed per amine functionality). The amount of trapped nitric oxide, following desorption, was determined to be 139 cm$^3$/g, equivalent to 6.2 mmol/g. These data collectively suggest chemisorption of the nitric oxide onto the primary amine functional groups within the UiO-66-NH$_2$ framework.

Example 3 IR Spectra of UiO-66-NH$_2$ Treated with Nitric Oxide

Figure 2:
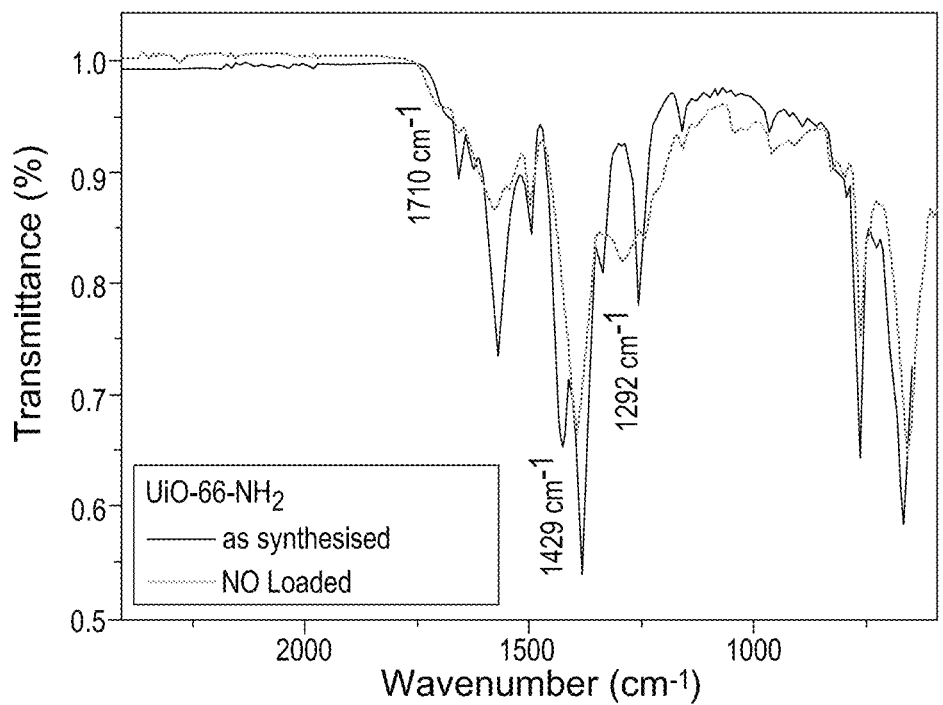
FIG. 2 shows the FTIR spectra of UiO-66-$NH_2$ before and after treatment under an atmosphere of nitric oxide at 10 bar.

FIG. 2 shows the Fourier-transform infrared (FTIR) spectra of UiO-66-NH$_2$ before and after treatment under an atmosphere of nitric oxide at 10 bar. The samples were removed from the pressure reactor as detailed in Example 1 before the spectra were measured. The spectrum of UiO-66-NH$_2$ previously treated under a pressurised nitric oxide atmosphere, revealed two new peaks at 1294 and 1710 cm$^{-1}$. These peaks can be assigned to the presence of N-diazeniumdiolate species, which form following the reaction of a primary amine with two equivalents of nitric oxide.

A peak at 1429 cm$^{-1}$ was observed in nitric oxide free UiO-66-NH$_2$, which can be assigned to a $v_{C-NH2}$ stretching mode coupled with $v_{C-C}$ ring modes. This peak was not observed in the spectra of UiO-66-NH$_2$ treated with nitric oxide.

These data support the formation of N-diazeniumdiolate species within the UiO-66-NH$_2$ framework through reaction of the primary amines therein with nitric oxide gas.

Example 4 Release of Nitric Oxide from UiO-66 and UiO-66-NH$_2$ Samples

The release of nitric oxide from the samples was measured in phosphate buffer saline (PBS, pH of 7.4) at room temperature. The concentration of nitric oxide released from the metal-organic frameworks was measured using a nitric oxide detection system (inNOII, Innovative instruments, Inc.) equipped with amiNO-700 electrodes. Each amiNO-700 electrode was calibrated prior to the experiment according to the manufacturer's instructions. Each sample (30 mg) was suspended in 25 mL of PBS buffer in a falcon tube equipped with a magnetic stirrer bar.

Figure 3:
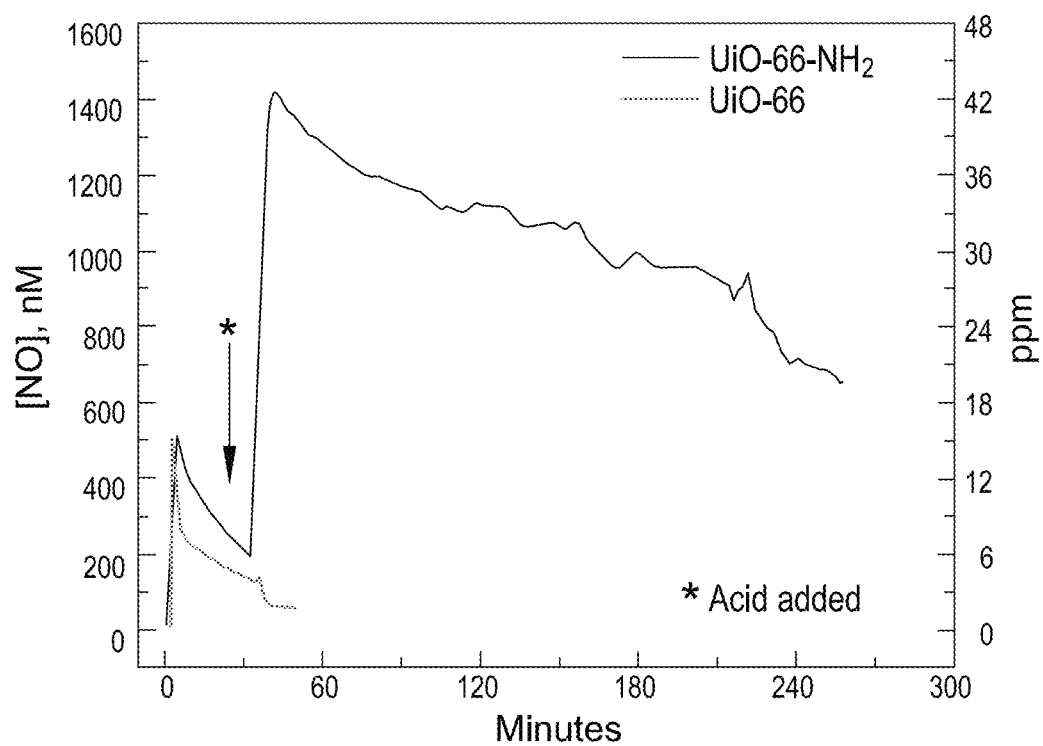
FIG. 3 shows nitric oxide release profiles in PBS and after addition of 0.1 mL of 1M $H_2SO_4$ to the PBS buffer for UiO-66 (green) and UiO-66-$NH_2$ (red)

FIG. 3 shows the concentration of nitric oxide released from UiO-66 and Ui-66-NH$_2$ samples previously treated under a high pressure atmosphere of nitric oxide. Both of the UiO-66 and UiO-66-NH$_2$ samples revealed an initial rapid increase in concentration of nitric oxide upon addition to the PBS solution. This initial rapid increase corresponds to the desorption of weakly adsorbed nitric oxide molecules within the metal-organic framework structure. Both the UiO-66 and UiO-66-NH$_2$ samples revealed similar nitric oxide concentration profiles over the first 30 minutes.

After 30 minutes, 0.1 mL of 1 M H$_2$SO$_4$ was added to each sample. A rapid increase in the concentration of nitric oxide was observed for UiO-66-NH$_2$, reaching a maximum nitric oxide concentration of 42 ppm. In contrast, no detectable increase in concentration of nitric oxide was observed for UiO-66 upon the addition of acid.

These data suggest the amine functionality within UiO-66-NH$_2$ is crucial to achieving chemisorption of nitric oxide molecules, potentially as N-diazeniumdiolates, within the metal-organic framework. As UiO 66 contains the same metal-carboxylate clusters as UiO-66-NH$_2$, the observed enhancement in the concentration of nitric oxide for UiO-66-NH$_2$ can be attributed to the presence of the amine functionality.

Figure 4:
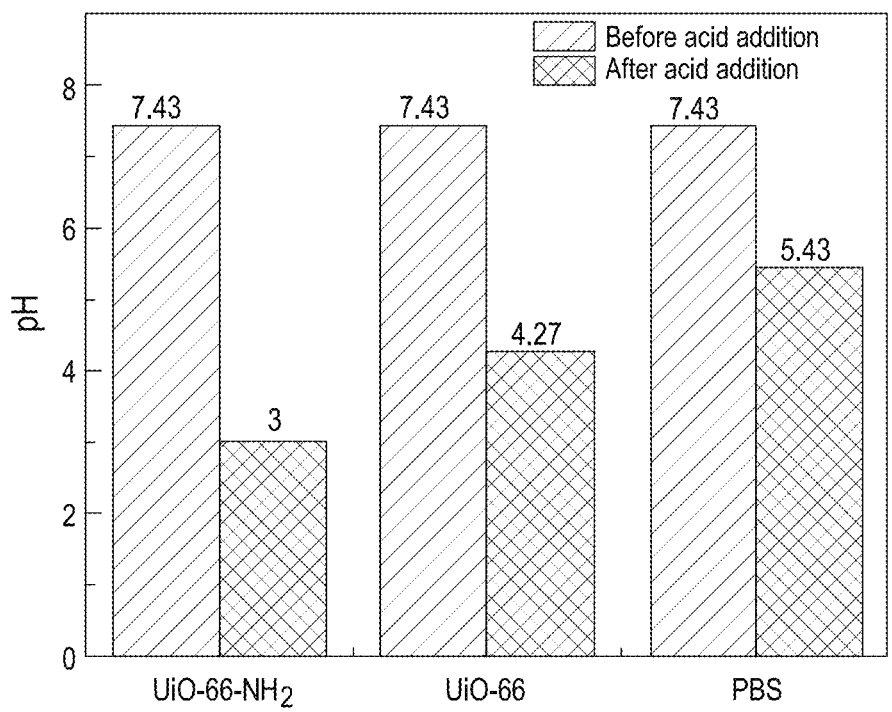
FIG. 4 shows the pH of the PBS buffer before and after the addition of 0.1 mL of 1M $H_2SO_4$ for UiO-66-$NH_2$, UiO-66 and PBS samples.

FIG. 4 shows the pH of each PBS sample before addition of acid, and at the completion of the experiment. For UiO-66-NH$_2$, the pH of the solution at the end of the experiment was determined to be 3, representing the largest decrease in pH for any of the samples investigated. Notably, addition of the acid solution to PBS alone resulted in a decrease in pH to only 5.4. Under aqueous conditions, nitric oxide may react with water and oxygen to produce nitrous acid. These data are therefore consistent with the observed high concentration of nitric oxide released into solution (FIG. 3).

These data also show that UiO-66-NH$_2$ enables an acid triggered release of nitric oxide. In turn, this provides a mechanism to control when and where nitric oxide is released, i.e. controlled release.

Example 5 X-Ray Powder Diffraction Patterns (PXRDs) of UiO-66 and UiO-66-NH$_2$

Figure 5:
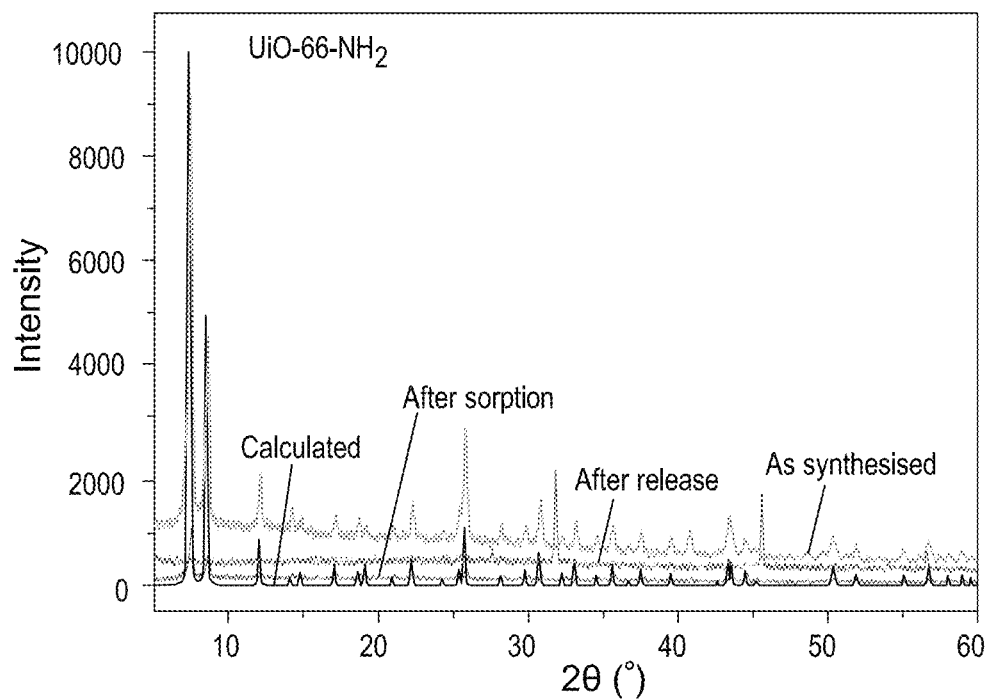
FIG. 5 shows the X-ray diffraction powder pattern of UiO-66-$NH_2$ (before and after treatment under a high pressure atmosphere of nitric oxide)
Figure 6:
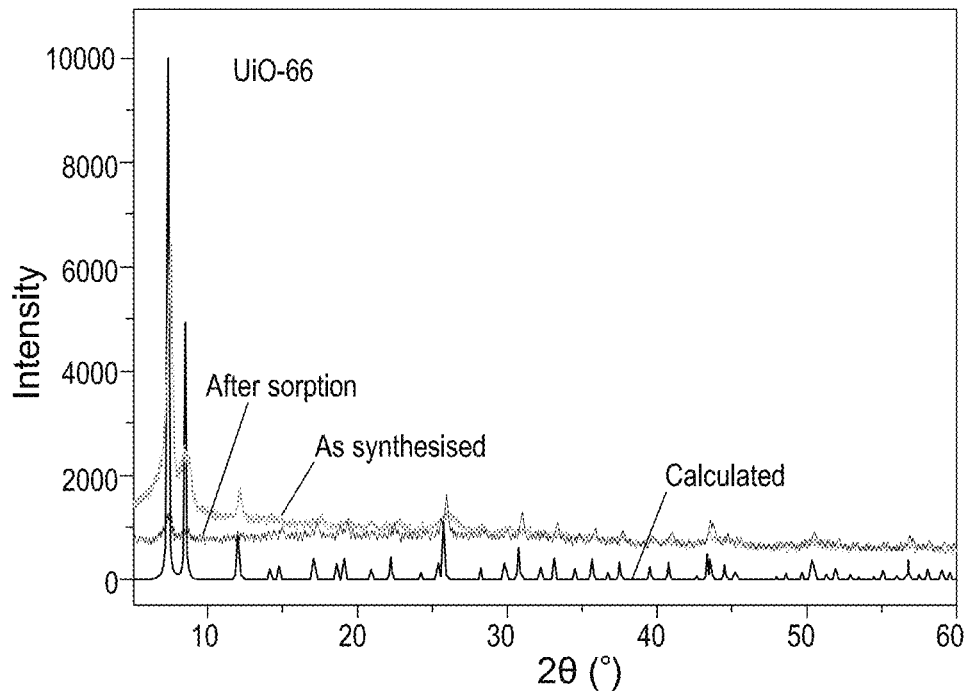
FIG. 6 shows the X-ray diffraction powder pattern of UiO-66 (before and after treatment under a high pressure atmosphere of nitric oxide)

FIGS. 5 and 6 show the PXRDs of UiO-66-NH$_2$ and UiO-66 respectively. These data indicate that the samples prepared have high levels of homogeneity and purity.

Example 7 IR Spectra of UiO-66-NH$_2$ and UiO-66-NH$_2$@Silica

Figure 7:
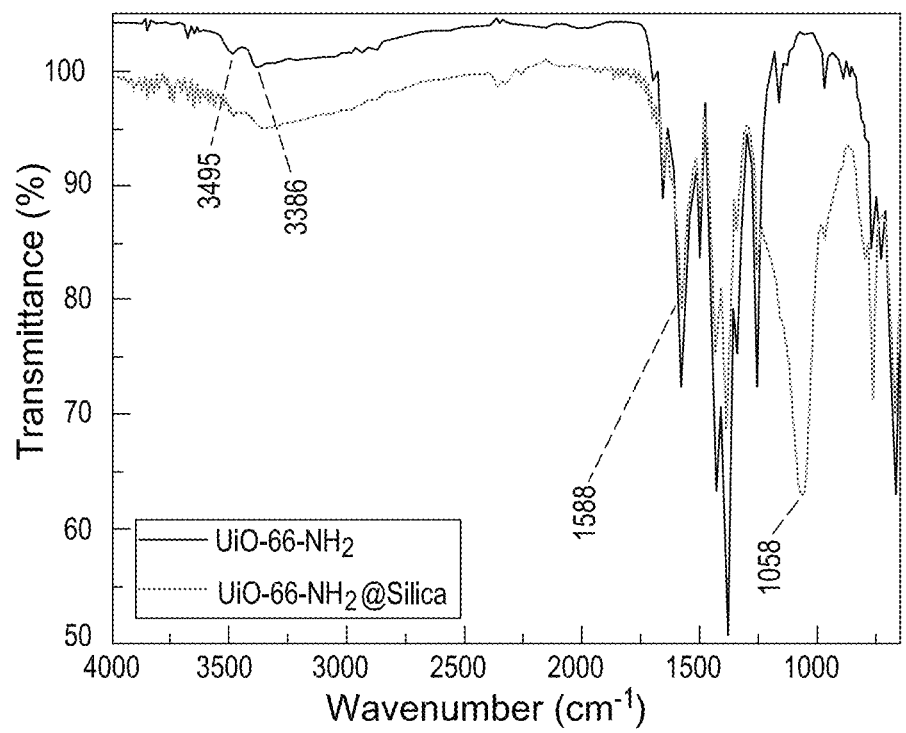
FIG. 7 shows the FTIR spectra of UiO-66-$NH_2$ and UiO-66-$NH_2$@silica.

FIG. 7 shows the FTIR spectrum of UiO-66-NH$_2$ and UiO-66-NH$_2$@silica. The spectra of UiO-66-NH$_2$@silica was found to be almost identical to that of UiO-66-NH$_2$, with the exception of an additional peak at 1058 cm$^{-1}$, which can be assigned to the silica Si—O stretching.

Example 8 Microporosity of UiO-66-NH$_2$ and UiO-66-NH$_2$@Silica

Figure 8:
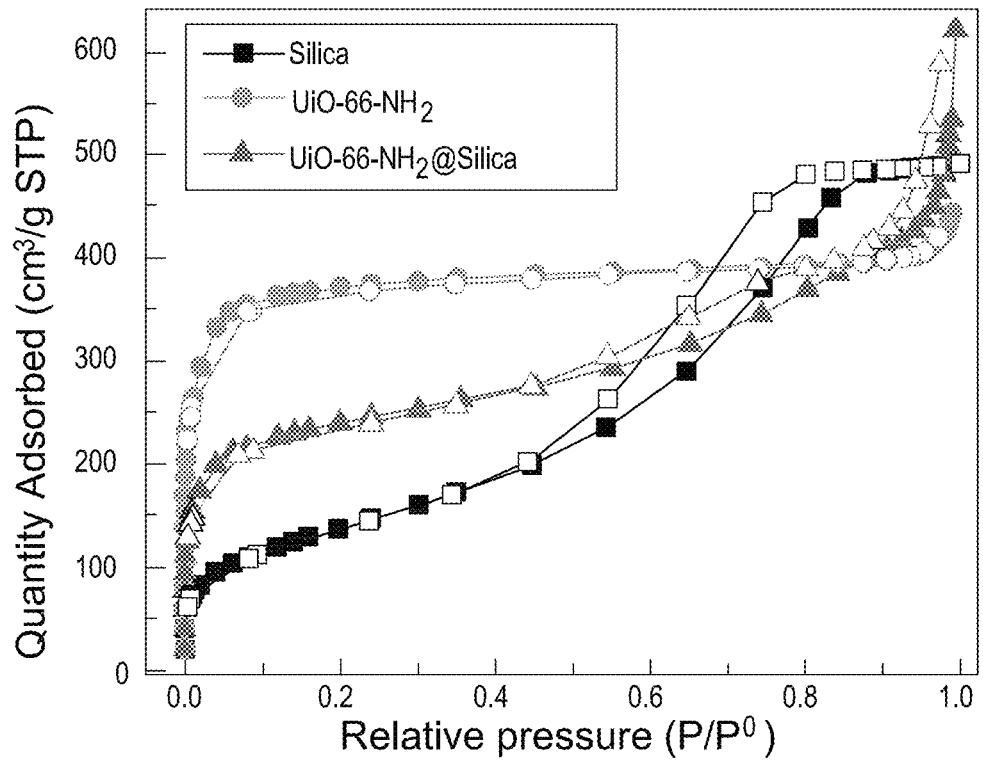
FIG. 8 shows $N_2$ isotherms of the UiO-66-$NH_2$, UiO-66-$NH_2$@Silica, and the silica support (closed symbols for adsorption, open for desorption)

The microporosity of UiO-66-NH$_2$@silica compared to UiO-66-NH$_2$ was investigated by determining the nitrogen gas isotherms for each sample (FIG. 8). Following determination of the N$_2$ gas isotherms, the Brauner-Emmet-Teller (BET) surface area for UiO-66-NH$_2$@silica and UiO-66-NH$_2$ were calculated (Table 2). The surface area of UiO-66-NH$_2$ was calculated as 1256 m$^2$/g. The calculated surface area for silica was 503 m$^2$/g. In contrast, the calculated surface area of UiO-66-NH$_2$@Silica, which comprised 48 wt % silica, was determined to be 730 m$^2$/g. These data indicate that the microporosity of the UiO-66-NH$_2$ metal-organic framework was maintained on the surface of the silica support.

TABLE 2

Calculated BET surface areas of UiO-66-NH$_2$@Silica, UiO-66-NH$_2$ and Silica support.

| Entry | Silica | UiO-66-NH$_2$ | UiO-66-NH$_2$@Silica |
|---|---|---|---|
| BET SA (m$^2$/g) | 503 | 1256 | 730 |

Figure 9:
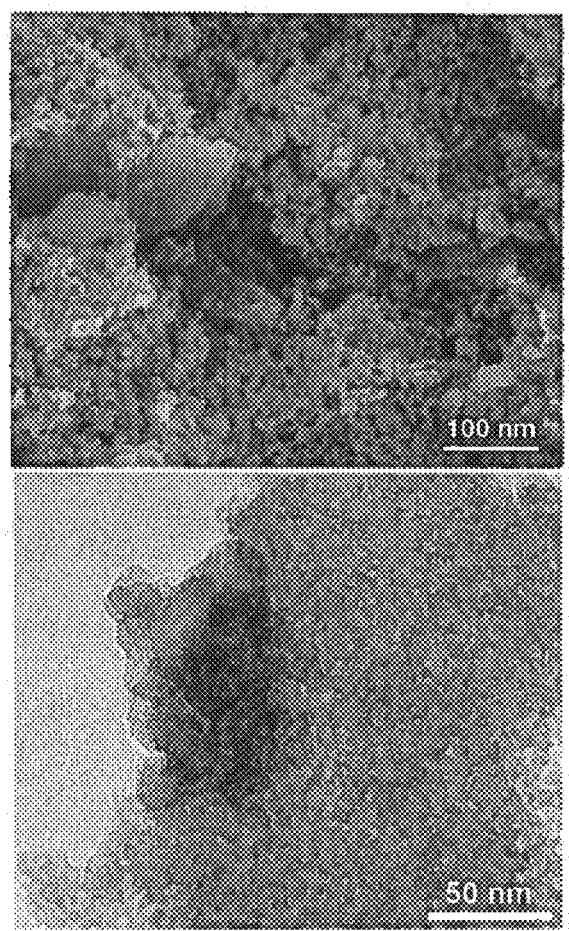
FIG. 9 shows SEM images of the UiO-66-$NH_2$@Silica showing complete coverage of the silica particles by the MOF (top) and the TEM image of the composite showing efficient compounding of the MOF nanoparticles grown on silica (bottom)

Example 9 Uniformity of UiO-66-NH$_2$ on the Surface of Silica in UiO-NH$_2$@Silica Scanning electron microscopy (SEM) and transmission electron microscopy (TEM) was used to investigate the morphology of UiO-66-NH$_2$ on the silica support surface. FIG. 9 (top image) shows an SEM image of UiO-66-NH$_2$@Silica, revealing homogenous distribution of the UiO-66-NH$_2$ crystals across the silica surface and complete coverage thereof. FIG. 9 (bottom image) shows a TEM image of UiO-66-NH$_2$@Silica revealing the tight attachment of UiO-66-NH$_2$ nanoparticles to the silica surface, and the uniform size distribution of the UiO-66-NH$_2$ nanoparticles (~20-30 nm diameter). The uniformity of the nanoparticles can be attributed to mechanical stirring of the growth solution under solvothermal conditions.

Figure 10:
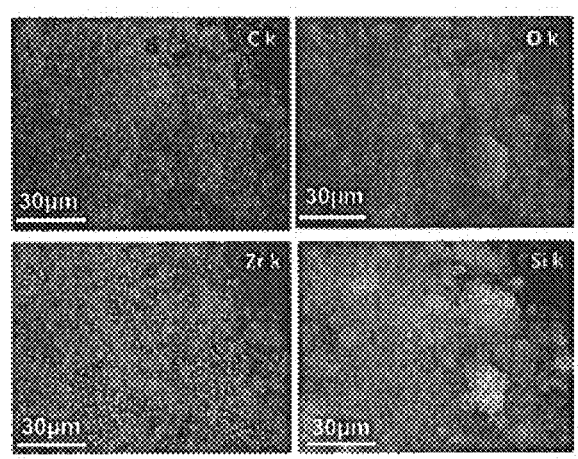
FIG. 10 shows EDX maps for the UiO-66-$NH_2$@Silica demonstrating homogenous distribution of the elements (labelled images) throughout the sample.

Energy-dispersive X-ray spectroscopy (EDX) was also used to confirm the homogeneous distribution of MOF onto the silica support. FIG. 10 shows the EDX spectra for UiO-NH$_2$@Silica, mapped for the presence of Carbon, Oxygen, Zirconium and Silicon. As can be seen from the elemental distribution, the UiO-66-NH$_2$ homogeneously covers the entirety of the silica surface.

Example 10 Elemental Analysis of UiO-66-NH$_2$ and UiO-NH$_2$@Silica

The composition of UiO-NH$_2$@Silica and UiO-66-NH$_2$ were further investigated by elemental analysis (Table 3). The Carbon and Nitrogen content for UiO-66-NH$_2$@Silica decreased compared to UiO-66-NH$_2$ due to the incorporation of silica. The observed increased Hydrogen content can be attributed to the presence of silanol groups and/or adsorbed moisture in the silica. The overall decrease in the total Carbon, Hydrogen and Nitrogen (CHN) content for UiO-66-NH$_2$@Silica can be attributed to the presence of the silica. The percentage weight of UiO-66-NH$_2$ within the UiO-66-NH$_2$@Silica composite was calculated to be 56 wt %. These data are in good agreement with that calculated based on the isolated yield of UiO-66-NH$_2$@Silica after synthesis.

TABLE 3

Elemental Analysis for the UiO-66-NH$_2$ and UiO-66-NH$_2$@Silica

| Compound | C (%) | N (%) | H (%) | Total |
|---|---|---|---|---|
| UiO-66-NH$_2$ | 28.60 | 4.11 | 2.77 | 35.49 |
| UiO-66-NH$_2$@Silica | 14.13 | 1.29 | 3.10 | 18.53 |

Example 11 X-Ray Powder Diffraction Pattern (PXRDs) of UiO-66-NH$_2$@Silica

Figure 11:
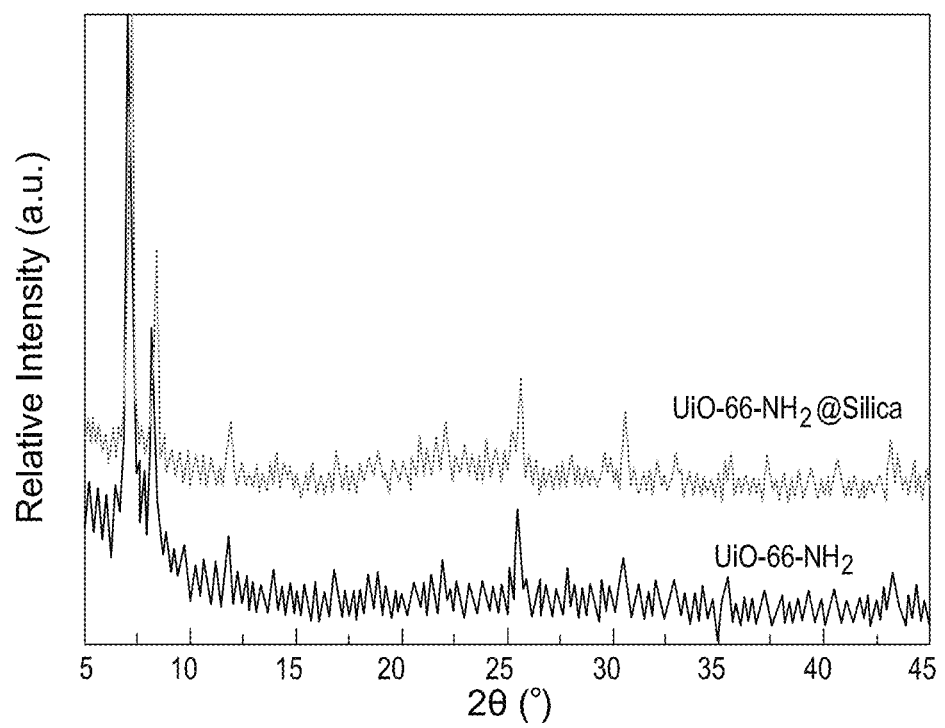
FIG. 11 shows the X-ray diffraction powder patterns for UiO-66-$NH_2$ and UiO-66-$NH_2$@silica.

FIG. 11 shows the PXRDs of UiO-66-NH$_2$ and UiO-66-NH$_2$@silica. The PXRDs observed for the UiO-66-NH$_2$@Silica corresponded to that of UiO-66-NH$_2$. These data further indicated the successful homogeneous formation of UiO-66-NH$_2$ on the silica surface.

The invention claimed is:

1. A nitric-oxide containing composite in the form of microparticles, wherein said microparticles comprise:
   (i) a core which comprises silica;
   (ii) a layer on said core which comprises a metal-organic framework; and
   (iii) nitric oxide;
   wherein said metal-organic framework comprises organic ligands of formula (III) comprising at least one amine group,

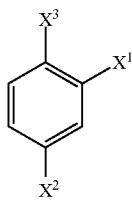

(III)

wherein $X^1$ is independently selected from $NH_2$ and NHR, wherein R is $C_{1-8}$ alkyl or $C_{5-10}$ aryl; and each of $X^2$ and $X^3$ are independently selected from COOH, OH, OR, SH, SR, $NH_2$, NHR, $NR_2$, $NO_2$, halide, $C_{1-6}$ alkyl, $OC_{1-6}$alkyl, $C_{5-10}$ aryl, heteroaryl, $SO_3R$ and $SO_3H$, wherein R is $C_{1-8}$ alkyl or $C_{5-10}$ aryl, and said metal-organic framework is uniformly distributed on the surface of said silica core, and completely covers the surface of said core, and said nitric oxide is chemisorbed within said metal-organic framework.

2. The composite as claimed in claim 1, wherein said metal-organic framework is in the form of nanocrystals having an average diameter of 1-200 nm.

3. The composite as claimed in claim 1, wherein said layer which comprises a metal-organic framework has a thickness of 5-100 nm.

4. The composite as claimed in claim 1, wherein said layer, which comprises a metal-organic framework, is a monolayer.

5. The composite as claimed in claim 1, wherein said core consists of silica.

6. The composite as claimed in claim 1, wherein said core has an average diameter of 1-200 μm.

7. The composite as claimed in claim 1, wherein each of $X^2$ and $X^3$ are independently selected from COOH, OH and $NH_2$.

8. The composite as claimed in claim 1, wherein each of $X^2$ and $X^3$ are COOH.

9. The composite as claimed in claim 1, wherein said organic ligands are of formula (IV):

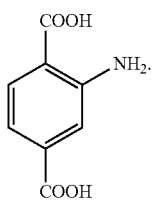

(IV)

10. The composite as claimed in claim 1, wherein said metal-organic framework further comprises a metal-containing secondary building unit comprising a metal selected from Zr, Hf, Ti, Zn, Cr, In, Ga, Cu, Fe, Mo, Cr, Co, Ru, Na, Mg, Mn, Ni, W, Al and V.

11. The composite as claimed in claim 10, wherein said metal is Zr.

12. The composite as claimed in claim 10, wherein said metal-containing secondary building unit is $Zr_6O_4(OH)_4$—$(CO_2)_{12}$.

13. The composite as claimed in claim 1, wherein said composite comprises 20-90 wt % silica.

14. The composite as claimed in claim 1, wherein said composite comprises 10-80 wt % metal-organic framework.

15. The composite as claimed in claim 1, wherein said microparticles have an average diameter of 1 to 250 μm.

16. The composite as claimed in claim 1, wherein said composite has a porosity of 100-2000 $m^2$/g.

17. A method of making a nitric-oxide containing composite as claimed in claim 1, comprising:

(i) mixing silica microparticles and precursors for the preparation of a metal-organic framework, wherein said precursors comprise metal ions and an organic ligand of formula (III) comprising at least one amine group to form a mixture;

(ii) stirring said mixture;

(iii) obtaining a composite in the form of microparticles, wherein said microparticles comprise a core which comprises silica and a layer on said core which comprises a metal-organic framework, wherein said metal-organic framework comprises an organic ligand of formula (III) comprising at least one amine group and said metal-organic framework is uniformly distributed on the surface of said silica core;

(iv) contacting said composite with nitric oxide under pressure; and (v) obtaining said nitric oxide-containing composite.

18. A pharmaceutical composition or dosage form comprising a composite as claimed in claim 1.

19. The composite as claimed in claim 1, wherein when the composite is exposed to pH of less than 6, NO is released from the metal organic framework.

* * * * *